United States Patent [19]

Steiger

[11] 4,453,928
[45] Jun. 12, 1984

[54] CATHETER TUNNELING APPARATUS

[75] Inventor: Ezra Steiger, Beachwood, Ohio

[73] Assignee: The Cleveland Clinic Foundation, Cleveland, Ohio

[21] Appl. No.: 376,529

[22] Filed: May 10, 1982

[51] Int. Cl.³ .................. A61M 5/00; A61M 25/00
[52] U.S. Cl. ................................. 604/53; 604/164; 604/264
[58] Field of Search .................... 604/49, 51–53, 604/158–170, 264; 128/303 R, 329

[56]  References Cited

U.S. PATENT DOCUMENTS

| | | | |
|---|---|---|---|
| 3,127,894 | 4/1964 | Smith | 604/51 |
| 3,670,729 | 6/1972 | Bennett et al. | 604/53 |
| 3,840,008 | 10/1974 | Noiles | 604/158 X |
| 4,014,333 | 3/1977 | McIntyre | 604/167 X |
| 4,147,164 | 4/1979 | Behney | 604/51 X |
| 4,299,228 | 10/1981 | Peters | 604/53 X |
| 4,327,722 | 5/1982 | Groshong et al. | 604/53 |

OTHER PUBLICATIONS

"A Modified Treatment for TPN Catheter Insertion" Nutritional Support Services, vol. 2, No. 2, Feb. 1982, pp. 44 & 47.

Primary Examiner—Dalton L. Truluck
Attorney, Agent, or Firm—Fay & Sharpe

[57]  ABSTRACT

The tunneling apparatus includes a body portion (A) with an elongated shaft (10) having a hollow passage (12) therethrough, a tube (B) slidably received on the shaft, and a syringe (C) connected with a trailing end of the hollow passage. The shaft has a blunt tip (14) with an outlet aperture (16) in fluid communication with the hollow shaft passage. The tube has a tapered leading end (30). In use, the tube is slidably received on the shaft with its tapered leading end adjacent the blunt tip and the syringe is filled with anesthesia. The shaft and tube are advanced under the patient's skin and, simultaneously, the syringe is operated to pump the anesthesia through the tip aperture to anesthetize the tissue adjacent the tip. After the subcutaneous tunnel is formed, the shaft and syringe are withdrawn leaving the tube below the skin to define the tunnel. A catheter is passed through the tube and the tube removed leaving the catheter subcutaneously positioned.

4 Claims, 3 Drawing Figures

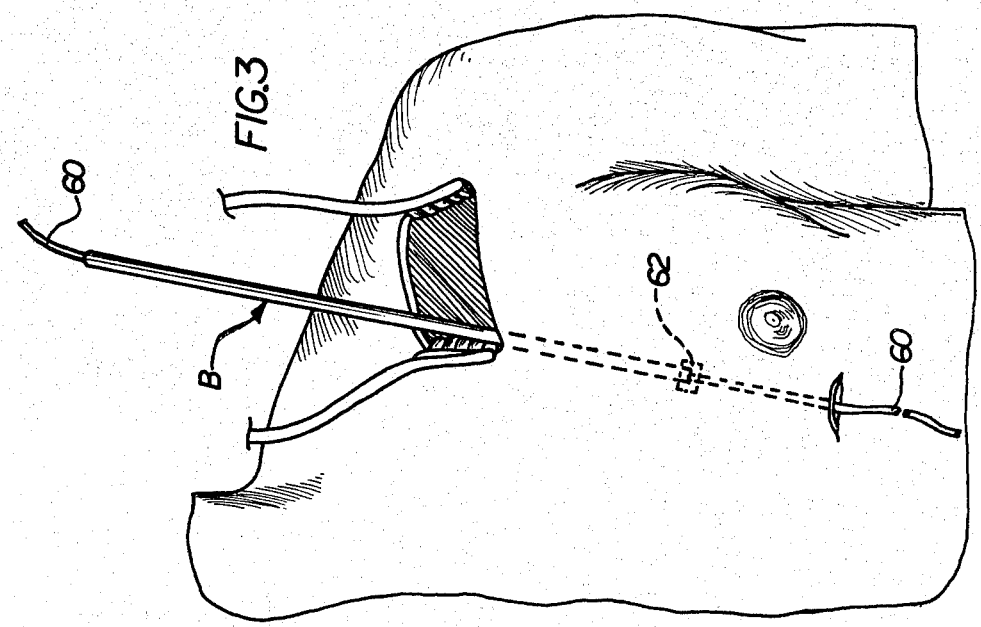
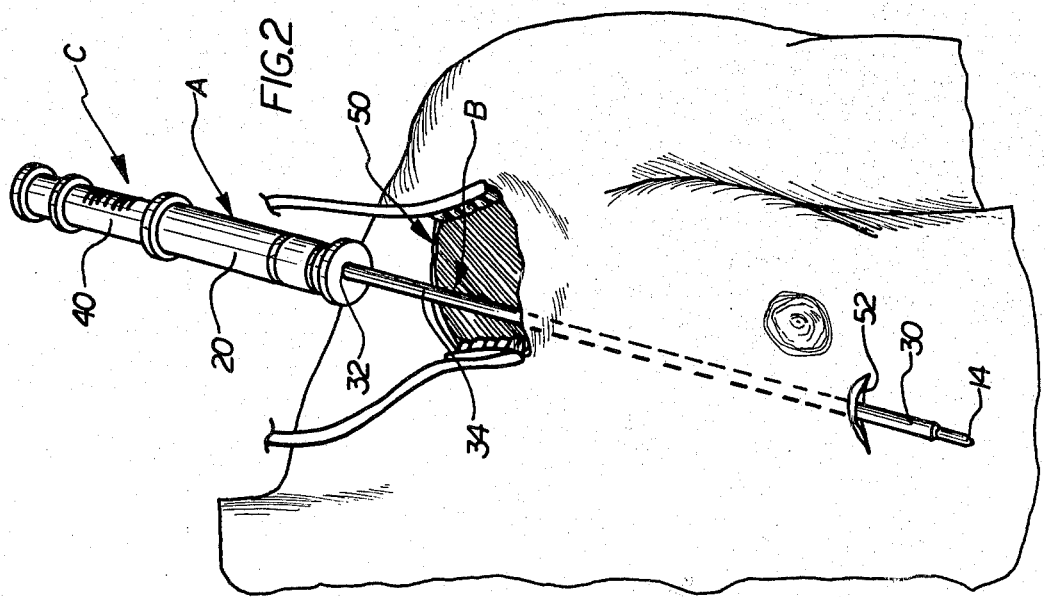

CATHETER TUNNELING APPARATUS

BACKGROUND OF THE INVENTION

This application pertains to the art of surgery and surgical instruments and more particular to an apparatus and method for subcutaneously inserting catheters. The invention finds particular application in conjunction with the insertion of catheters in the cephalic vein through the subclavian area for introducing parenteral nutrition, antibiotics, chemotherapy, and the like. It is to be appreciated, however, that the invention finds further application for creating tunnels through and between various body tissues.

Heretofore, catheters were inserted in the cephalic vein through a cut-down site through the chest wall over the vein. Multiple injections of anesthesia were made through the skin along a proposed tunnel path from the cut-down site to the parasternal border at the level of the nipple. An ovum-seeking forceps or other elongated forceps, was inserted at the cut-down site and manually urged along the tunnel path thus separating the skin from the underlying tissue to form the subcutaneous tunnel. The end of the forceps exited through an incision at the parasternal border to grasp an end of the catheter. The catheter was then drawn by the forceps through the tunnel to the cut-down site. The catheter was then inserted through venotomy in the cephalic vein and positioned such that its tip lay in the superior vena cava.

One of the most uncomfortable parts of the catheter insertion procedure, which is often done under local anesthesia, was the creation of the subcutaneous tunnel.

The present invention contemplates a new and improved tunneling apparatus and procedure which reduces the patient discomfort and forms the subcutaneous channel more simply and precisely.

SUMMARY OF THE INVENTION

In accordance with the present invention, there is provided a tunneling instrument for creating a subcutaneous tunnel which includes an axial shaft, a pump means operatively connected with one end of the shaft, and a tube slidably received on the shaft. The axial shaft has a hollow, longitudinally extending passage extending therethrough to a rounded, blunt tip at one end. The tip is adapted to separate the tissue as the shaft is advanced to create the subcutaneous channel. The tip defines at least one outlet aperture therethrough in fluid communication with the hollow passage for permitting local anesthesia to pass from the hollow passage to the tissue being separated. The pump means is operatively connected with the hollow passage for selectively pumping anesthesia through the hollow passage and the outlet aperture into the tissue. The tube is slidably mounted on the shaft in such a manner that upon creating the subcutaneous tunnel, the shaft is adapted to be slidably removed from the tube leaving the tube between the separated tissue to define the tunnel.

In accordance with another aspect of the invention, there is provided a method for creating a subcutaneous tunnel. the method includes inserting a shaft with a hollow tube slidably received thereon through tissue. As the shaft is advanced, anesthesia is pumped through the shaft and into the tissue adjacent the leading end of the shaft. The leading end of the shaft and the hollow tube exit from the tissue. The shaft is slidably removed from the tube. A catheter or other tubing is passed through the tube and the tube is slidably removed from the tissue positioning the catheter in the subcutaneous tunnel.

A primary advantage of the present invention is that it reduces patient discomfort during the creation of a subcutaneous tunnel.

Another advantage of the present invention is that it precisely creates subcutaneous tunnels of a relatively small bore.

Another advantage of the present invention is that it simplifies and facilitates the subcutaneous placement of catheters.

Still further advantages of the present invention will become apparent to others upon reading and understanding the following detailed description of the preferred embodiment.

BRIEF DESCRIPTION OF THE DRAWINGS

The invention may take form in various parts and arrangements of parts and in various steps and arrangements of steps. The drawings illustrate a preferred embodiment of the invention only and are not to be construed as limiting the invention.

FIG. 2 illustrates a tunneling apparatus in accordance with the present invention forming a subcutaneous tunnel from the a cut-down site above the cephalic vein to an incision at the parasternal border; and, FIG. 3 illustrates a method of using the tunneling apparatus of FIG. 1 for inserting a catheter.

DETAILED DESCRIPTION OF THE PREFERRED EMBODIMENT

Figure 1:
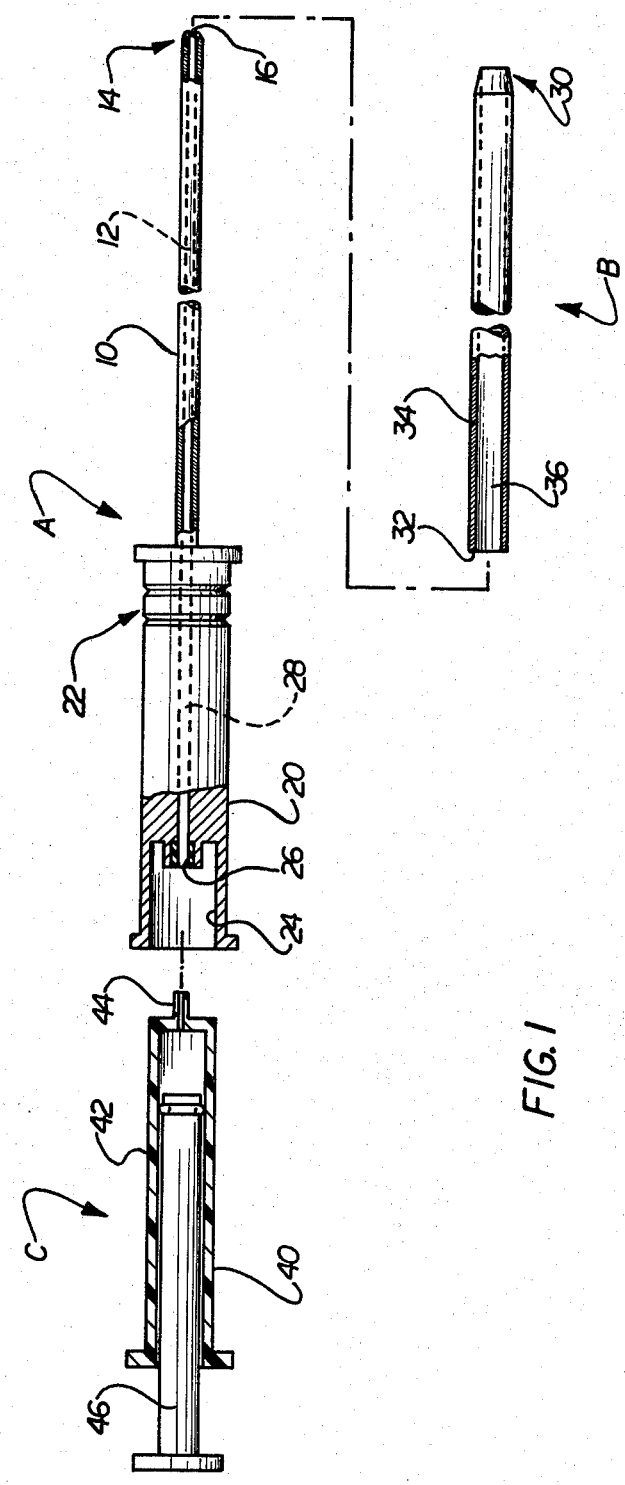
FIG. 1 is an exploded view of a tunneling apparatus in accordance with the present invention.

The tunneling apparatus includes a body portion A which slidably receives a tube B and is adapted to be connected with a syringe or other pumping means C.

The body portion A includes an elongated stainless steel shaft 10 having a diameter at least equal to and preferably greater than the diameter of a catheter which is to be inserted. The shaft 10 includes a hollow, longitudinally elongated passage or bore 12 which extends therethrough. At a leading end, the shaft has a blunt tip 14 which is adapted to separate tissue, particularly the skin tissue from the underlying muscle tissue, to form a tunnel therethrough. The shaft tip is sufficiently tapered that separation of the tissue is facilitated, yet sufficiently blunt that impaling or piercing of the skin or underlying muscle tissue is inhibited. At least one outlet aperture 16 is formed through the tip in fluid communication with the hollow passage. The outlet aperture may be a jet-like opening which releases fluids forward with a relatively high velocity, a larger diameter opening which allows fluids to flow therethrough at a relatively low velocity, a plurality of pores or perforations which allow sufficient fluids to pass therethrough that the tip remains moist, or the like.

Adjacent a trailing end, the shaft 10 is connected with a syringe holder or other connecting means 20. A compression fitting or the like 22 connects the shaft and the syringe holder. A syringe receiving bore 24 is adapted to receive the syringe C in a firm frictional relationship. A fluid sealing means 26 provides a fluid tight seal between the syringe and a hollow bore 28 which is in fluid communication with the shaft hollow passage 12.

The tube B has a tapered leading end 30 to facilitate tissue separation as it advances therethrough and a trailing end 32 which is adapted to abut the syringe holder 20. The tube is constructed with a thin stainless steel wall 34 and an internal bore 36 having a diameter which is the same as or slightly larger than the diameter of the shaft 10. The fit between the shaft and tube should be snug at least adjacent the leading end 30, yet sufficiently loose that the shaft and tube can be slidingly disengaged with relative ease. The length of the tube relative to the length of the shaft is such that the tapered tube leading end 30 is closely adjacent the blunt tip 14 of the shaft to form a relatively smooth expanding outside diameter therewith.

The pumping means C, in the preferred embodiment, is a syringe 40 which is received directly in the connecting means 20. The syringe includes a syringe body 42 having volumetric gradiations thereon and a fluid outlet 44 which is adapted to be received in a fluid tight seal with the sealing means 26. A plunger 46 is disposed in the syringe barrel to be manual advanced therealong to pump fluid, particularly an anesthesia, therefrom. Alternately, the pumping means may be located remote from the connecting means 20 and be connected by a flexible tubing. Further, the pumping means may include a selectable rate pump which pumps the anesthesia automatically at a selectable rate.

With reference to FIG. 2, in use, the tube B is slidably received on the shaft 10 with its trailing end 32 firmly abutting the connecting means 20 and the syringe 40 is received in the connecting means with a fluid tight seal. A cut-down site 50 is made in the patient's chest over the cephalic vein. The shaft tip 14 of the tunneling apparatus is positioned below the skin at the lower end of the cut-down site. The syringe is advanced to pump a small amount of Xylocaine, or other anesthesia, through the shaft passage and out the aperture 16 to anesthetize the area of the patient adjacent the shaft tip 14. The shaft tip 14 and tube leading end 30 are slowly advanced forming the subcutaneous tunnel. As the shaft tip is advanced, the syringe plunger is advanced at a coordinated rate, continuously or intermittently as is appropriate, to maintain the area surrounding the tip anesthetized. The shaft tip and tube leading end are directed to an exit site, specifically through an incision 52 at the parasternal border at the level of the nipple. The tube B remains in this location as the shaft is withdrawn toward the cut-down site and removed.

With reference to FIG. 3, after withdrawal of the shaft, the tube B protrudes from the cut-down site and the exit incision and defines a hollow tunnel therebetween. A catheter 60 is inserted from the leading end 30 of the tube and out the trailing end 32 until a dacron-velour cuff 62 rests against the leading end. The catheter and tube are pulled simultaneously through the tunnel and out the cut-down site until the dacron-velour cuff lies midway between the exit site and cut-down site. The catheter is then held in place and the hollow tube is withdrawn from the patient, leaving the catheter in the subcutaneous tunnel. The catheter is trimmed to the appropriate length and inserted in a venotomy incision in the cephalic vein. The catheter is directed into the superior vena cava under fluoroscopy.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A method of creating a subcutaneous tunnel between skin and muscle tissue of a patient, the method comprising:
   inserting a shaft which has a longitudinal passage therethrough and which terminates at a shaft leading end in a tip which is sufficiently tapered to separate the muscle and skin tissue and sufficiently blunt to inhibit impaling and piercing of the skin and muscle tissues into an internal bore of a thin walled tube such that the shaft tip extends beyond the thin walled tube;
   inserting the shaft tip under the patient's skin adjacent an entrance site;
   pumping anesthesia through the shaft passage and out of the shaft tip into the muscle and skin tissue thereadjacent;
   advancing the shaft and the tube between the patient's muscle and skin tissue while pumping anesthesia therethrough at a coordinated rate which maintains the muscle and skin tissue adjacent the tip anesthetized as the shaft and tube form the tunnel between the skin and muscle tissues;
   exiting the shaft tip and a leading end of the tube through an exit incision at an exit site completing the tunnel between the entrance and exit sites;
   withdrawing the shaft from the tube while retaining the tube between the skin and muscle tissues to define a mechanical tunnel between the entrance and exit sites;
   passing a flexible catheter through the tube such that the catheter extends from both ends thereof;
   partially withdrawing the tube and catheter together; and,
   fully withdrawing the tube while substantially retaining the catheter against further withdrawal.

2. The method as set forth in claim 1 further including trimming the end of the catheter adjacent the entrance site and inserting the trimmed end of the catheter in a patient's cephalic vein.

3. A tunneling apparatus for creating a mechanical, subcutaneous tunnel comprising:
   an elongated, flexible catheter having an external velour cuff generally centrally therealong for being received in the tunnel to inhibit the catheter from moving relative to the tunnel;
   a tube extending linearly between a tube leading end and a tube trailing end, the tube having a constant internal cross-section therethrough which is dimensioned for slidably receiving said elongated, flexible catheter therethrough, the tube being externally tapered at the tube leading end to facilitate separation of tissue as the tube advances therethrough;
   a shaft having a hollow, longitudinal passage extending therethrough between a shaft leading end and a shaft trailing end, the shaft having a tip at the shaft leading end which is sufficiently tapered to facilitate separation of tissue and sufficiently blunt that impaling and piercing of skin and underlying muscle tissue is inhibited, the shaft having an external diameter which is at least as large as the diameter of the flexible catheter, the shaft exceeding the length of the tube and being slidably received therein with the tip extending beyond the tube leading end;

a syringe holder operatively connected with the shaft trailing end, the syringe holder having a hollow bore therethrough in fluid communication with the shaft passage at one end and having a fluid sealing means at its other end for providing a fluid-tight seal with a syringe, the syringe holder defining a syringe receiving bore for receiving an exterior surface of the syringe to assist in maintaining a fluid-tight seal between the syringe and the fluid sealing means;

anesthesia pumping means for pumping anesthesia through the syringe holder bore and shaft passage into the tissue adjacent the shaft tip for supplyng anesthesia to tissue adjacent the tip as the tip is advanced between skin and muscle tissue creating the tunnel, the anesthesia pumping means including the syringe which is received in the syringe receiving bore and the fluid sealing means.

4. A method of creating a subcutaneous tunnel between skin and muscle tissue of a patient, the method comprising:

inserting a shaft which has a longitudinal passage therethrough and which terminates at a shaft leading end in a tip which is sufficiently tapered to separate the muscle and skin tissue and sufficiently blunt to inhibit impaling and piercing of the skin and muscle tissues into an internal bore of a thin walled tube such that the shaft tip extends beyond the thin walled tube;

inserting the shaft tip under the patient's skin adjacent an entrance sites;

pumping anesthesia through the shaft passage and out of the shaft tip into the muscle and skin tissue thereadjacent;

advancing the shaft and the tube between the patient's muscle and skin tissue while pumping anesthesia therethrough at a coordinated rate which maintains the muscle and skin tissue adjacent the tip anesthetized as the shaft and tube form the tunnel between the skin and muscle tissues;

exiting the shaft tip and a leading end of the tube through an exit incision at an exit sites completing the tunnel between the entrance and exit sites;

withdrawing the shaft from the tube while retaining the tube between the skin and muscle tissues to define a mechanical tunnel between the entrance and exit sites;

inserting a flexible catheter which has a cuff and is longer than the tube through the tube internal bore from the tube leading end until the cuff abuts the tube leading end;

withdrawing the tube and catheter through the entrance sites, until the cuff is disposed subcutaneously between the entrance and exit sites;

withdrawing the tube fully through the entrance sites and from the catheter while holding the catheter against being withdrawn with the tube.

* * * * *